United States Patent [19]

Christensen et al.

[11] Patent Number: 4,997,936
[45] Date of Patent: * Mar. 5, 1991

[54] 2-CARBAMIMIDOYL-6-SUBSTITUTED-1-CARBADETHIAPEN-2-EM-3-CARBOXYLIC ACIDS

[75] Inventors: Burton G. Christensen, Cliffside Park; David B. R. Johnston, Warren; Susan M. Schmitt, Scotch Plains, all of N.J.

[73] Assignee: Merck & Co., Inc., Rahway, N.J.

[*] Notice: The portion of the term of this patent subsequent to Feb. 12, 2008 has been disclaimed.

[21] Appl. No.: 898,887

[22] Filed: Aug. 21, 1986

Related U.S. Application Data

[63] Continuation of Ser. No. 368,788, Apr. 15, 1982, abandoned, which is a continuation-in-part of Ser. No. 197,856, Oct. 17, 1980, which is a continuation-in-part of Ser. No. 129,851, Mar. 27, 1980, abandoned, which is a continuation-in-part of Ser. No. 31,694, Apr. 19, 1979, abandoned, and a continuation-in-part of Ser. No. 207,042, Nov. 14, 1980, which is a continuation-in-part of Ser. No. 134,381, Mar. 27, 1980, abandoned, which is a continuation-in-part of Ser. No. 933,681, Aug. 17, 1978, abandoned, which is a continuation-in-part of Ser. No. 843,378, Oct. 19, 1977, abandoned, and a continuation-in-part of Ser. No. 206,935, Nov. 14, 1980, which is a continuation-in-part of Ser. No. 134,604, Mar. 27, 1980, abandoned, which is a continuation-in-part of Ser. No. 843,375, Oct. 19, 1977, abandoned.

[51] Int. Cl.$^5$ .................... C07D 487/04; A61K 31/40
[52] U.S. Cl. ........................ 540/350; 514/210
[58] Field of Search ...................... 540/310, 350

[56] References Cited

U.S. PATENT DOCUMENTS

| 4,309,346 | 1/1982 | Christensen et al. | 260/245.2 T |
|---|---|---|---|
| 4,309,438 | 1/1982 | Christensen et al. | 260/245.2 T |
| 4,312,871 | 1/1982 | Christensen et al. | 260/245.2 T |
| 4,335,043 | 6/1982 | Christensen et al. | 260/245.2 T |
| 4,341,706 | 7/1982 | Christensen et al. | 260/245.2 T |
| 4,347,368 | 8/1982 | Christensen et al. | 260/245.2 T |
| 4,552,873 | 11/1986 | Myadra et al. | 540/350 |
| 4,696,923 | 9/1987 | Christensen et al. | 540/350 |
| 4,720,490 | 1/1988 | Mak et al. | 514/210 |

Primary Examiner—Nicholas S. Rizzo
Attorney, Agent, or Firm—Raymond M. Speer; Hesna J. Pfeiffer

[57] ABSTRACT

Disclosed are 2- and 6-substituted-1-carbadethiapen-2-em-3-carboxylic acids having the structure:

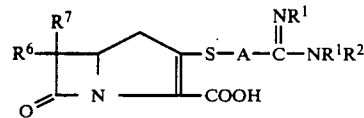

wherein $R^6$, and $R^7$ are, inter alia, independently selected from the group consisting of hydrogen, alkyl, alkenyl, aryl and aralkyl; A is a direct, single bond connecting the indicated S and C atoms, or A is a cyclic or acyclic connecting group selected, inter alia, from alkyl, cyclalkyl, aryl, heteroaryl, heteroalkyl; $R^1$ and $R^2$ inter alia, independently selected from hydrogen, alkyl, aryl; additionally, said carbamimidoyl is characterized by cyclic structures achieved by the joinder of the two nitrogen atoms via their substituents and by their joinder to connecting group A; additionally, "carbamimidiums" are disclosed by quarternization of one of the nitrogen atoms of said carbammidoyl. Such compounds as well as their pharmaceutically acceptable salt, ester and amide derivatives are useful as antibiotics. Also disclosed are processes for the preparation of such compounds; pharamaceutical compositions comprising such compounds; and methods of treatment comprising administering such compounds and compositions when an antibiotic effect is indicated.

1 Claim, No Drawings

2-CARBAMIMIDOYL-6-SUBSTITUTED-1-CAR-BADETHIAPEN-2-EM-3-CARBOXYLIC ACIDS

BACKGROUND OF THE INVENTION

This is a continuation of application Ser. No. 368,788, filed Apr. 15, 1982, now abandoned, which is a continuation-in-part U.S. patent application Ser. No. 197,856 filed Oct. 17, 1980 which is a continuation-in-part of U.S. patent application Ser. No. 129,851, filed Mar. 27, 1980, now abandoned, which is a continuation-in-part of U.S. patent application Ser. No. 31,694 filed Apr. 19, 1979, now abandoned; it is also a continuation-in-part of U.S. patent application Ser. No. 207,042 filed Nov. 14, 1980 which is a continuation-in-part of U.S. patent application Ser. No. 134,381 filed Mar. 27, 1980 now abandoned, which is a continuation-in-part of U.S. Ser. No. 933,681 filed Aug. 17, 1978, now abandoned, which is a continuation-in-part of U.S. Ser. No. 843,378 filed Oct. 19, 1977, now abandoned; and U.S. patent application Ser. No. 206,935 filed Nov. 14, 1980 which is a continuation-in-part of U.S. patent application Ser. No. 134,604 filed Mar. 27, 1980, now abandoned which is a continuation-in-part of U.S. Ser. No. 843,375 filed Oct. 19, 1977, now abandoned.

This invention relates to 2- and 6-substituted-1-carbadethiapen-2-em-3-carbxylic acids (I) and the pharmaceutically acceptable salt, ester and amide derivatives theref which are useful as antibiotics:

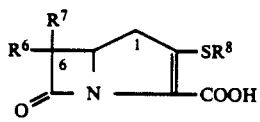

wherein $R^6$ and $R^7$ are independently selected from the group consisting of: hydrogen; substituted and unsubstituted: alkyl, alkenyl, and alkynyl, having from 1–10 carbon atoms; cyclalkyl, cycloalkylalkyl and alkylcycalkyl, having 3–6 carbon atoms n the cycloalkyl ring and 1–6 carbon atoms in the alkyl moieties; aryl such as phenyl; aralkyl, aralkenyl, and aralkynyl wherein the aryl moiety phenyl and the aliphatic portion has 1–6 carbon atoms; heteroaryl, heteroaralkyl, heteroalkyl, heterocyclyl and heterocyclylalkyl; wherein the heteroatom or atoms are selected from O, N and S; wherein the substituent or substituents on $R^6$ and $R^7$ are independently selected from carboxyl, mercapto, amino, mono- and disubstituted amino wherein the substituent is alkyl having from 1–6 carbon atoms, chloro, fluoro, bromo, hydroxy, alkylthio having 1–6 carbon atoms and alkoxyl having 1–6 carbon atoms; additionally $R^6$ and $R^7$ may be joined to form, together with the carbon atom to which they are attached, a cyclicalkyl having 3–6 carbon atoms.

$R^8$ is generically defined to be a "carbamimidoyl", which may be defined by the following structures:

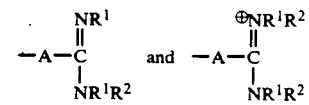

wherein A, the cyclic or acyclic connecting group, and $R^1$ and $R^2$ are defined below. The definition of $R^8$ also embraces cyclic structures, which may be generically represented, for example, thusly:

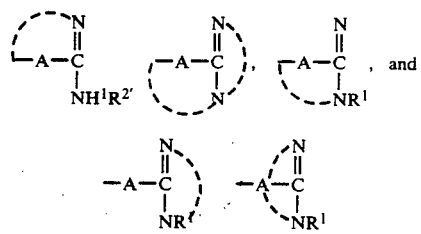

wherein the dotted lines indicate that the nitrogen atoms of the so called carbamimidoyl function may participate in the formation of the cyclic structures indicated above. Representative specific embodiments for $R^8$ (as well as $R^6$ and $R^7$) follow, but, in the generic sense, the components: $R^1$, $R^2$ and A which comprise $R^8$ are defined, thusly:

A, the cyclic or acyclic connector, is selected from the group consisting of alkyl, alkenyl, and alkynyl having 1–10 carbon atoms which may be interrupted by a hetero atom selected from O, S or N, or by a ring such as phenyl, cycloalyl, cycloalkenyl, heterocyclyl or heteroaryl wherein such cyclic interruptions comprise 3–6 ring atoms selected from C, O, S and N; cycloalkyl, cycloalkenyl having 3–6 carbon atoms; heterocyclyl; heteroaryl; and phenyl; A also represents a direct, single bond connecting the indicated S and C atoms.

$R^1$ and $R^2$ are independently selected from hydrogen and the previously defined values for the group A, such as: alkyl, aryl, cycloalkyl, heteroalkyl, alkylaryl, alkylarylalkyl, and heterocyclyl and heteroaryl.

It should be noted that the final products of this invention (I) can exist in either neutral or zwitterionic (internal salt) forms. In the zwitterionic form, the basic function is protonated and positively charged and the carboxyl group is deprotonated and negatively charged. The zwitterionic form is the predominant species under most conditions and is in equilibrium with a minor amount of the uncharged, neutral species. The equilibrium process is conveniently visualized as an internal acid-base neutralization. The neutral and zwitterionic forms are shown below.

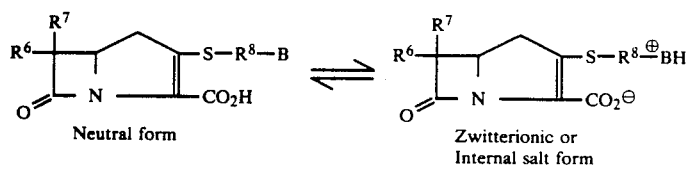

Neutral form    Zwitterionic or Internal salt form wherein B is the carbamimidoyl group.

Further, the final products of this invention I wherein $R^8$ contains a positively charged quaternary nitrogen function such as the "carbamimidinium" can exist as zwitterionic (internal salt) forms or as external salt forms. The preferred form of this product group is the zwitterionic or internal salt form. These forms are shown below:

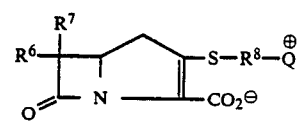

Zwitterionic (internal salt) form

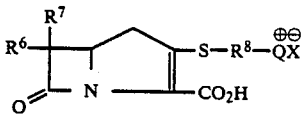

External salt form wherein Q represents the quarternized nitrogen group, and wherein X is a pharmaceutically acceptable anion such as those listed in U.S. Pat. No. 4,194,047, issued Mar. 18, 1980, which is incorporated herein by reference.

This invention also relates to the carboxyl derivatives of I which are antibiotics and which may be represented by the following generic structure (1):

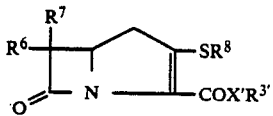

wherein X' is oxygen, sulphur or NR' (R'=H or lower alkyl having 1-6 carbon atoms); and $R^{3'}$ is, hydrogen, or, inter alia is representatively selected to provide the pharmaceutically acceptable salt, ester, anhydride ($R^{3'}$ is acyl), and amide moieties known in bicyclic β-lactam antibiotic art; $R^{3'}$ may also be a readily removable blocking group. The definition of $R^{3'}$ is given in greater detail below.

This invention also relates to processes for the preparation of such compounds I; phamaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both Gram positive bacteria such as *S. aureus, Strep. pyogenes,* and *B. subtilis,* and Gram negative bacteria such as *E. Coli,* Pseudomonas, *Proteus morganii,* Serratia, and Klebsiella. Further objects of this invention are to provide chemical processes for the preparation of such antibiotics and their nontoxic, phamaceutcally acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

DIAGRAM I

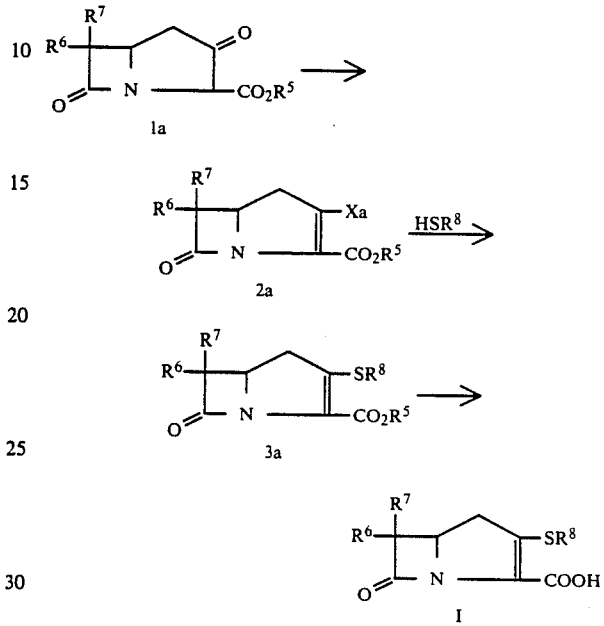

In words relative to the above reaction scheme, Diagram 1, the step 1a to 2a to establish leaving group $X^a$ is accomplished by acylating the bicyclic keto ester 1a with an acylating agent $RX^a$ such as p-toluenesulfonic acid anhydride, p-nitrophenylsulfonic acid anhydride, 2,4,6-triisopropylphenylsulfonic acid anhydride, methanesulfonic acid anhydride, trifluoromethane sulfonic acid anhydride, diphenyl chlorophosphate, toluenesulfonyl chloride, p-bromophenylsulfonyl chloride, or the like; wherein $X^a$ is the corresponding leaving group such as toluene sulfonyloxy, p-nitrophenylsulfonyloxy, benzenesulfonyloxy, diphenylphosphoryl, and other leaving groups which are established by conventional procedures and are well known in the art. Typically, the above acylation to establish leaving group Xa is conducted in a solvent such as methylene chloride, acetonitrile or dimethylformamide, in the presence of a base such as diisopropylethylamine, triethylamine, 4-dimethylaminopyridine or the like at a temperature of from −20° to 40° for from 0.1 to 5 hours. The leaving group $X^a$ of intermediate 2a can also be halogen. The halogen leaving group is established by treating 1a with a halogenating agent such as $O_3PCl_2$, $O_3PBr_2$, $(OO)_3PBr_2$, oxalylchloride or the like in a solvent such as $CH_2Cl_2$, $CH_3CN$, THF, or the like in the presence of a base such as diisopropylethylamine, triethylamine, or 4-dimethylaminopyridine or the like. [φ=phenyl.]

The reaction 2a to 22 is accomplished by treating 2a in a solvent such as dioxane, dimethylformamide, dimethylsulfoxide, acetonitrile, hexamethylphosphoramide, or the like, in the presence of an approximately equivalent to excess of the mecaptan reagent $HSR^8$, wherein $R^8$ is defined above, in the presence of a base such as sodium hydrogen carbonate, potassium carbonate, triethylamine, diisopropylethylamine, or the like at a temperature of from −40° to 25° C. for from 30 sec. to 1 hour.

The final deblocking step 22 to I is accomplished by conventional procedures such as solvolysis or hydogenation. The conditions of deblocking 22 to I are thus: typically 22 in a solvent such as tetrahydrofuran-water, tetrahydrofuran-ethanol-water, dioxane-water, dioxane-ethanol-water, n-butanol-water, or the like containing pH 7 mopholinopopanesulfonic acid-sodium hydroxide buffer, pH 7 phosphate buffer, dipotassium hydrogen phosphate, sodium bicarbonate, or the like, is treated under a hydrogen pressure of from 1 to 4 atmospheres in the presence of a catalyst such as platinum oxide, palladium on charcoal, or palladium hydroxide on charcoal, or the like, at a temperature of from 0° to 50° C. for from 0.25 to 4 hours to provide I. Photolysis, when $R^5$ is a group such as o-nitrobenzyl, for example, may also be used for deblocking.

Relative to Diagram I, the bicyclic keto ester 1a may be obtained by a variety of schemes of total synthesis. One of these schemes wherein $R^7$ is hydrogen and $R^6$ is hydroxyethyl (1a):

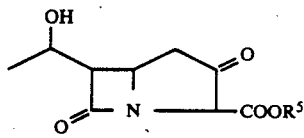

1a is disclosed in European Patent Application Number 79101307.1 filed May 1, 1979, publication number 0007973 (Feb. 20, 1980). This application is incorporated herein by reference, particularly to the extent that it describes the preparation of this embodiment of starting material 1a and its activation to 2a, in the context of the reactive scheme: 1a→2a →22→I.

The bicyclic keto ester 1a, in the general case, may be prepared by the processes disclosed and claimed in the three following, co-pendng, commonly assigned U.S. Patent Applications of Christensen, Ratcliffe and Salzmann. To the extent that these applications disclosed processes for the preparation of 1a, in its general expression,

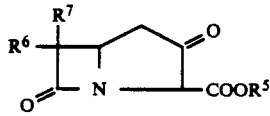

1a and the process scheme for the preparation of antibiotics I of the present invention according to the reactive scheme 1a→2a→22→I, they are hereby incorporated by reference. The three applications are:

(1.) Process for the Preparation of 1-Carbapenems and Intermediates via 4-Allylazetidinone; U.S. patent application Ser. No. 134,408 filed Mar. 27, 1980; European Patent Application 81102268.0 filed Mar. 26, 1981.

(2.) Process for the Preparation of 1-Carbapenems and Intermediates via Trithioorthoacetates; U.S. patent application Ser. No. 134,396 filed Mar. 27, 1980; European Patent Application 81102269.8 filed Mar. 26, 1981.

(3.) Process for the Preparation of 1-Carbapenems and Intermediates via Silyl-Substituted Dithioacetals; U.S. patent application Ser. No. 134,397 filed Mar. 27, 1980; European Patent Application 81102270.6 filed Mar. 26, 1981.

HSR[8] REAGENTS

Relative to the foregoing description of the invention, suitable carbamimidoyl and carbamimidinium mercaptans HSR[8] which are utilized in the transformation 2a to 22 are listed below. Wherein $R^8$ is:

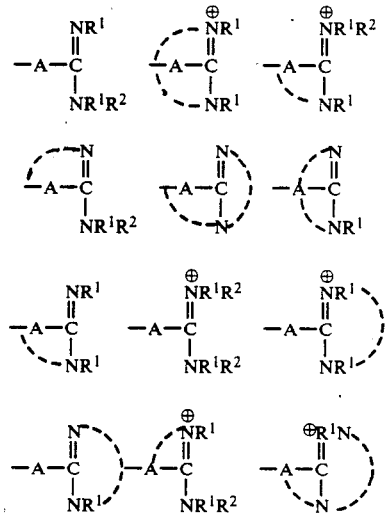

and wherein $R^1$ and $R^2$ are as initially defined under $R^8$; the two nitrogen atoms demonstrated in the above structure may participate in cyclic structures which are indicated by the dotted lines; A is a connecting group between the sulfur atom and carbamimidoyl function. It should be noted that while not all canonical forms of $R^8$ are reproduced herein, the foregoing list is representative and constitutes together with the associated text a definition of the "carbamimidoyl" group of the present invention.

$R^1$ and $R^2$ are independently selected from the group consisting of hydrogen; substituted and unsubstituted: straight and branched alkyl having from 1 to 6 carbon atoms; cycloalkyl wherein the cycloalkyl moiety comprises 3 to 6 carbon atoms and the alkyl moiety comprises 1 to 6 carbon atoms; alkylcycloalkyl wherein alkyl moiety comprises 1 to 6 carbon atoms and the cycloalkyl moiety comprises 3 to 6 carbon atoms; aryl such as phenyl; arylalkyl such as benzyl; heterocyclyl (saturated and unsaturated) comprising mono- and bicyclic structures having from 5 to 10 ring atoms, wherein one or more of the heteroatoms is selected from oxygen, nitrogen, or sulfur, such as thiophene, imidazole, tetrazolyl, furyl, pyridine; heterocycloalkyl groups which comprise the immediately preceding heterocyclyl moieties and the alkyl moiety comprises from 1 to 6 carbon atoms. The substituent or substituents relative to the above-named radicals comprising $R^1$ and $R^2$ are selected from the group consisting of amino, hydroxy, cyano, carboxyl, nitro, chloro, bromo, fluoro, alkoxy, and alkylthio having from 1 to 6 carbon atoms, mercapto, perhaloalkyl having 1 to 3 carbon atoms, guanidino, amidino, sulfamoyl. When located on the same nitrogen atom, the substituents $R^1$ and $R^2$ can be joined to form a cyclic group comprising 3-8 atoms. The resulting ring can contain additional O, S, or N atoms. For example: $-NR^1R^2$ may be:

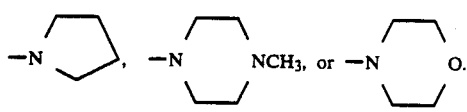

Particularly preferred groups under the definition of $R^1/R^2$ are: hydrogen; substituted and unsubstituted: straight and branched loweralkyl having from 1 to 6 carbon atoms; cycloalkyl having from 3 to 6 carbon atoms, cycloalkylalkyl wherein the cycloalkyl moiety comprises 3 to 6 carbon atoms and the alkyl moiety comprises 1 to 6 carbon atoms; aryl such as phenyl, arylalkyl such as benzyl; the substituents on the above-named radicals are selected from fluoro, hydroxy, mercapto, alkoxy and alkylthio having from 1 to 3 carbon atoms.

In defining the bivalent, cyclic or acyclic connector group "A", it is to be noted that the recited radicals of definition are to be read both left to right and right to left. Thus, the preferred connecting groups "A" are selected from; substituted and unsubstituted: loweralkyl having from 1–6 carbon atoms; cycloalkyl having from 3–10 atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; loweralkenyl having from 2–10 carbon atoms, cycloalkenyl having from 3 to 10 carbon atoms, cycloalkenylalkyl wherein the cycloalkenyl moiety comprises 3 to 10 carbon atoms; and the alkyl moiety comprises 1 to 6 carbon atoms; alkynyl having from 2 to 10 carbon atoms; aryl such as phenyl and naphthyl; arylalkyl and alkylaryl such as benzyl, phenethyl and the like; heteroalkyl, alkylheteroalkyl, arylheteroalkyl and alkylheteroaryl wherein the hetero atoms are selected from the group of sulfur, oxygen and nitrogen, the alkyl moiety has 1 to 6 carbon atoms, and the aryl moiety is phenyl; heterocyclyl (saturated and unsaturated) comprising mono- and bicyclic structures having 5 to 10 ring atoms wherein one or more of the hetero atoms is selected from oxygen, nitrogen, or sulphur such as thiophene, imidazole, pyridine, furyl and the like; heterocyclylalkyl wherein heterocyclyl moiety comprises from 3 to 10 atoms and the alkyl moiety comprises from 1 to 6 atoms; the substituent (or substituents) relative to the above-named radicals are selected from the group consisting of amino, hydroxyl, cyano, carboxyl, nitro, chloro, bromo, fluoro, alkoxy having from 1 to 6 carbon atoms, mercapto, perhaloloweralkyl such as trifluoromethyl and alkylthio having from 1–6 carbon atoms.

A particularly preferred class of connecting groups "A" are selected from: substituted and unsubstituted: straight and branched loweralkyl having from 1 to 6 carbon atoms, cycloalkyl having from 3 to 6 carbon atoms; phenyl; heterocyclyl such as thiophene, imidazole, pyridine, and furane; alkylheteroalkyl wherein alkyl moiety comprises 1 to 3 carbon atoms and the hetero atoms are sulfur, oxygen and nitrogen; the substituents relative to the above-named radicals are: amino, hydroxyl, chloro, bromo, fluoro, cyano, carboxyl, alkoxy having from 1 to 3 carbon atoms, mercapto, trifluoromethyl, and alkylthio having from 1 to 3 carbon atoms.

Also a preferred identity for "A" is as a single direct bond connecting the indicated sulfur and imidoyl function.

Prepresentative examples of such preferred $-SR^8$ groups (represented as $HSR^8$) are:

EXAMPLES

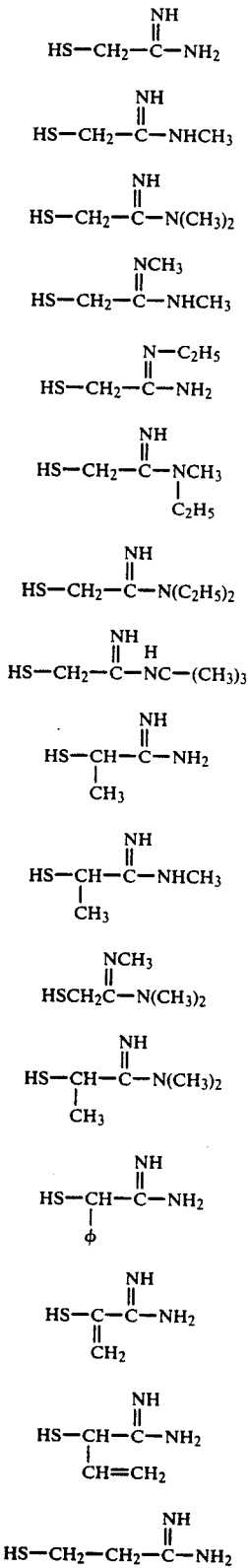

-continued

HS-CH₂-C(=NH)-NH₂ with OCH₃ on central C

HSCH₂-CH(OH)-C(NH₂)=NH₂... [structure with NH₂ and NH₂]

HS-CH₂-C(=N-OCH₃)-NH₂ (with NH on top)

HS-CH₂-CH(N(CH₃)₂)-C(=NH)-NH₂

HSCH₂-C(CO₂H)(=NH... )-N(CH₃)₂ [HSCH₂-C(CO₂H)-C(=NH)-N(CH₃)₂]

HS-CH(SCH₃)-C(=NH₂)-NH₂

HSCH₂-C(=NH)-NHφ

HS(CH₂)ₙ-C(=NR²)-NHR¹    n = 2–5, R² = H, CH₃
                          R¹ = H, CH₃

HSCH₂-C(CH₃)₂-C(=NH)-NH₂

HS-(CH₂)ₙ-C(=NR²)-NR¹R²    n = 2–5, R¹, R² = H, CH₃

HS-(CH₂)₂-S-CH₂-C(=NH)-N(CH₃)₂

HS-(CH₂)₂-O-CH₂CH₂-C(=NH)-NH₂

HS-C(CH₃)₂-C(=NH)-NH₂

HS-C(CH₃)₂-CH₂-C(=NH)-NH₂

HS-CH(CH₃)-CH₂-S-C(=N-H)-N(CH₃)₂

-continued

HSCH=CH-C(=NH)-N(CH₃)₂

HS-CH₂CH₂-C(=NH)-N(CH₃)₂

HSCH₂-C(=N-)(NH-) [2-mercaptomethyl-4,5-dihydroimidazole]

HSCH₂-C(=N-)(N(CH₃)-) [N-methyl dihydroimidazole]

HSCH₂CH₂-C(=NH)-HNC(CH₃)₃

[N-methylpyrrolidine ring with HS and =NCH₃ substituents]

HS-CH₂-C(=NH)-NH-CH(CH₃)₂

HS-CH₂-C(=NH)-N(pyrrolidinyl)

HSCH₂-C(=NH)-N(morpholinyl)

HSCH₂-C(=NH)-N(aziridinyl)

HSCH₂-C(=N-cyclopropyl)-N(CH₃)₂

HSCH₂-C(=NH)-N(piperidinyl)

11 12
-continued -continued
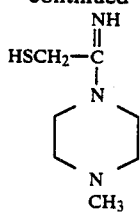
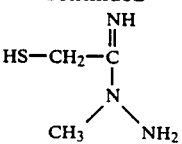
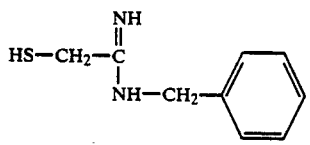
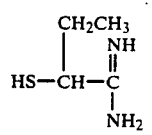
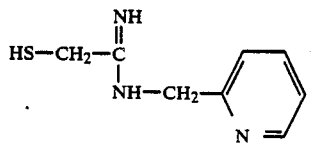
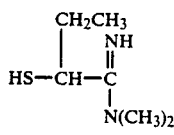
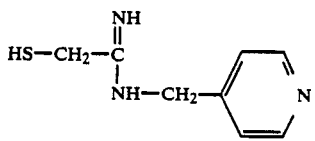
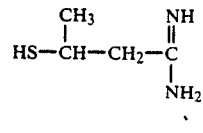
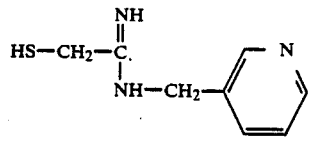
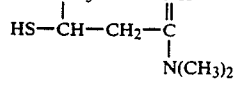
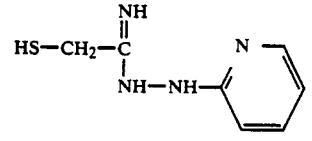
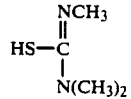
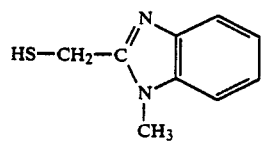
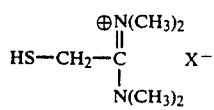
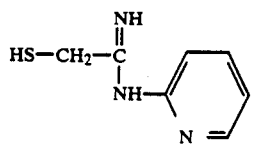
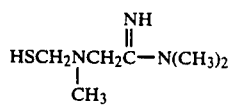
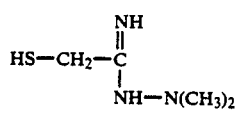
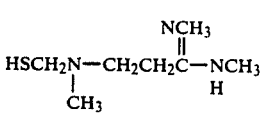
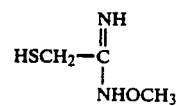
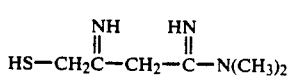
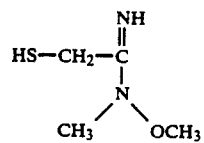
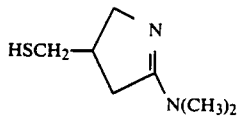
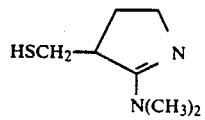
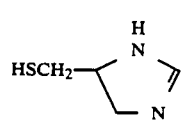

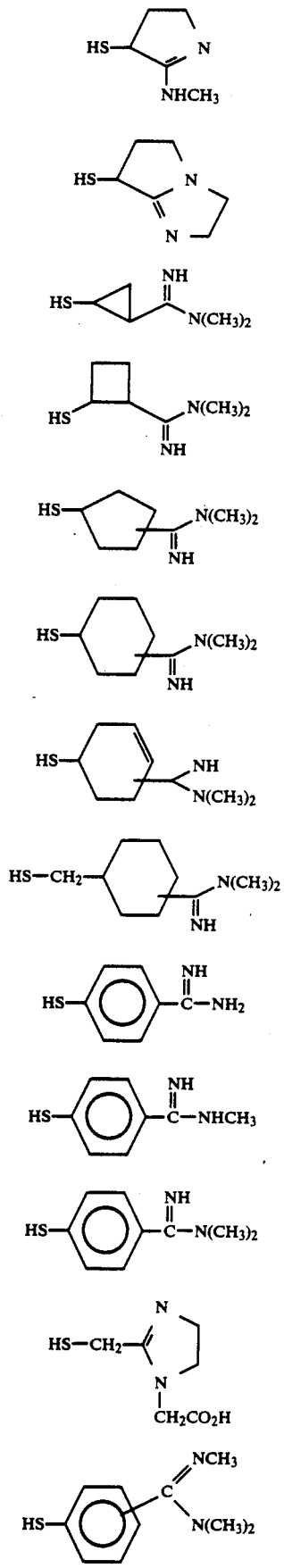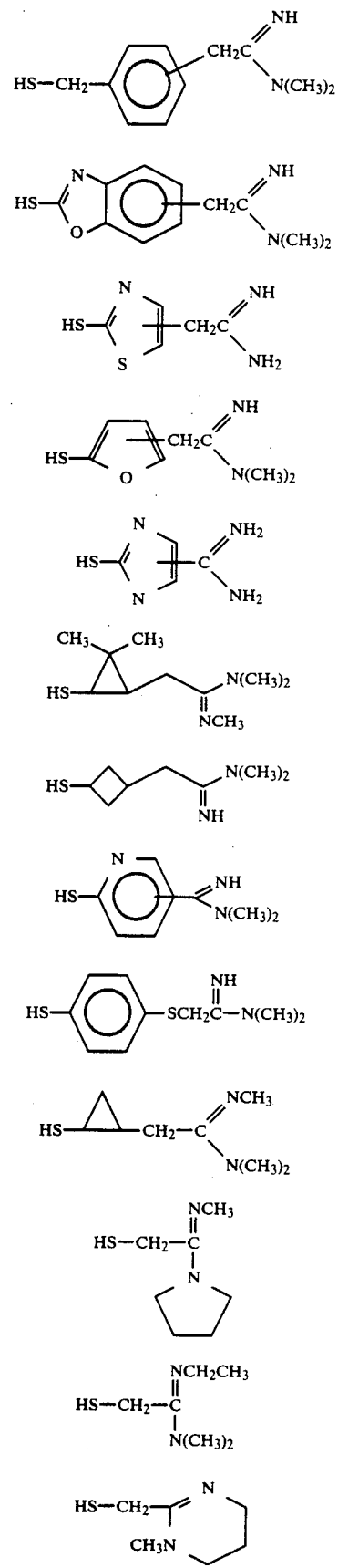

-continued

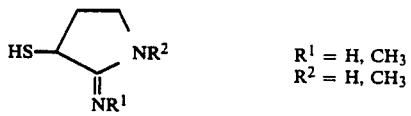 R¹ = H, CH₃
R² = H, CH₃

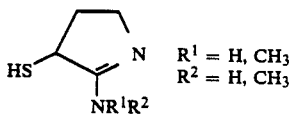 R¹ = H, CH₃
R² = H, CH₃

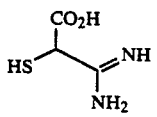

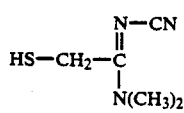

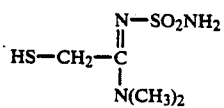

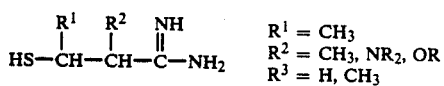 R¹ = CH₃
R² = CH₃, NR₂, OR
R³ = H, CH₃

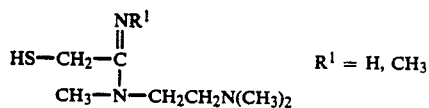 R¹ = H, CH₃

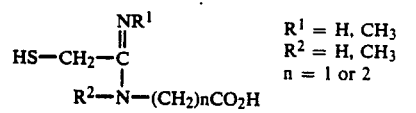 R¹ = H, CH₃
R² = H, CH₃
n = 1 or 2

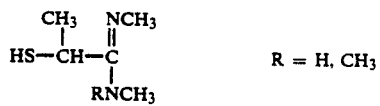 R = H, CH₃

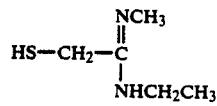

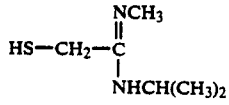

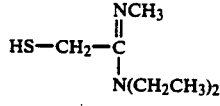

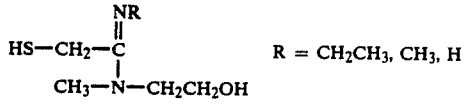 R = CH₂CH₃, CH₃, H

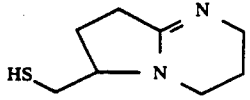

-continued

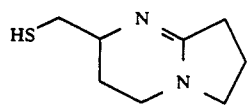

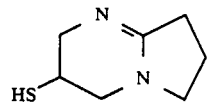

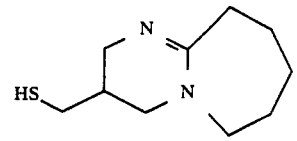

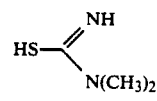

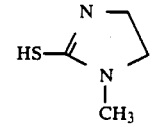

Relative to the foregoing, representative list of suitable reagents $HSR^8$, it should be noted that when the mercaptan contains a functional group which might interfere with the intended course of reaction, the offending group is covered. For example, when a basic nitrogen group is encountered (—NHR or —NH₂, for example) it is usually protected by acylation (e.g., —CO₂PNB) and when a carboxyl group (—CO₂H) is present, it is usually protected by esterification (e.g., PNB ester). Such protection also facilitates in the purification of products by chromatographic means. (PNB is p-nitrobenzyl.) Such protection is, however, not a necessary requirement for introduction of the —SR⁸ side chain. The transformation 2a→22 (Diagram I) is conveniently carried out using both protected and unprotected $HSR^8$ forms. It is recognized that $SR^8$ side chains in which the R group contains one or more chiral centers can be added as racemic or diastereomeric mixtures to provide mixtures of diastereomeric products or can be added as resolved, isomerically pure reagents to provide diastereomerically pure products. Since antibacterial activity and other pharmacological properties vary among isomers, it is frequently advantageous to prepare isomerically pure products by the introduction of resolved —SR⁸ side chains.

ALKYLATING AND ACYLATING REAGENTS FOR ESTABLISHING R⁶ AND R⁷ AND PREFERRED VALUES FOR R⁶ AND R⁷

As shown above, the compounds of the present invention (I) are conveniently prepared from starting material 1a, Diagram I. The following section describes the establishment of R⁶ and R⁷ upon other azetidinones which are also useful in the synthesis of compounds of the present invention. In this regard, see European Patent Application Serial Number 80102076.9 filed Apr. 18, 1980, which is fully incorporated herein by reference, particularly to the extent that it describes the azetidinone starting materials which are summarized below.

DIAGRAM II
(Scheme I)

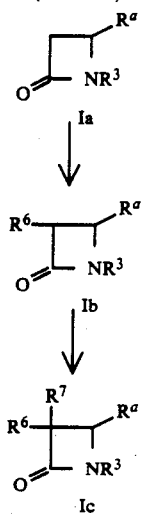

wherein:
(1) $R^a$ is $CH_2CH_2OR^2$; $R^3$ and $R^2$ are as defined in European Patent Application Serial Number 80102076.9;
(2) $R^a$ is $CH=CH_2$; see European Patent Application Serial Number 80102076.9;
(3) $R^a$ is $CH_2CH=CH_2$, see previously incorporated by reference U.S. Ser. No. 134,408, filed Mar. 27, 1980; European Patent Application 81102268.0 filed Mar. 26, 1981;
(4) $R^a$ is $CH_2C(SR^*)_3$, $R^*$ values are selected from alkyl, aryl, and aralkyl; see previously incorporated by reference U.S. Ser. No. 154,190, filed May 29, 1980; and U.S. Ser. No. 134,396, filed Mar. 27, 1980; European Patent Application 81102269.8 filed Mar. 26, 1981; and
(5) $R^a$ is $CH_2C(SR^*)_2SiR^*_3$, $R^*$ values are selected from alkyl, aryl and aralkyl; see previously incorporated by reference U.S. Ser. No. 134,397, filed Mar. 27, 1980, European Patent Application filed Mar. 26, 1981.

In words relative to the above reaction diagram, and as described above, starting material Ia can be mono-, or dialkylated at ring position 3. Alkylation of Ia provides Ic. Typically, Ia is treated with a strong base such as lithium diisopropylamide, lithium 2,2,6,6-tetramethylpiperidide, potassium hydride, lithium hexamethyldisilazane, phenyllithium or the like in a solvent such as tetrahydrofuran (THF), hexamethylphosphoramide, ether, dimethoxyethane, and the like at a temperature of from $-80°$ C. to $0°$ C. whereupon the alkylating agent of choice, $R^6X^*$ is added ($X^*$ is chloro, iodo or bromo); alternatively the alkylating agent may be $R^6$-tosylate, $R^6$-mesylate or an aldehyde or ketone such as acetaldehyde to provide monoalkylated species Ib. When desired, dialkylated species Ic may be obtained from Ib by repeating the alkylating procedures Ia→Ib.

The eventual 6-substituents (nomenclature relative to final, bicyclic structure) can also be established by direct acylation using an acylating agent such as N-acyl imidazole or the like. Such N-acyl imidazole acylating reagents are listed below. Also given below is a detailed description of this second approach for establishing, $R^6$ and $R^7$.

The following list is representative of useful agents for establishing $R^6$ and $R^7$, according to the above scheme Ia→Ib→Ic (this will be referred to as Scheme I, to be distinguished from Scheme II, below, which involves acylation):

Alkylating Agents
$CH_3CHO$
$\phi CH_2CHO$    $\phi$ = phenyl
$\phi CH_2CH_2CHO$
$CH_2O$
$CH_3I$
$\phi CH_2Br$
$CH_3COCH_3$

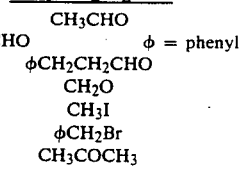

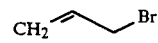

$CH_3OCH_2CHO$
$CH_3CH_2I$
$(CH_3)_2CHI$
$N_3CH_2CHO$
$(CH_3)_2NCH_2CHO$ $RO_2CCH_2Br$     R = $CH_3$, benzyl, p-nitrobenzyl
$CF_3CF_2CHO$
$RO_2CCH_2CHO$     R = $CH_3$, benzyl, p-nitrobenzyl
$CH_3CH(CH_3)CHO$,
$CH_3(CH_3)CHCH_2CHO$,
$CH_3CH_2CHO$,

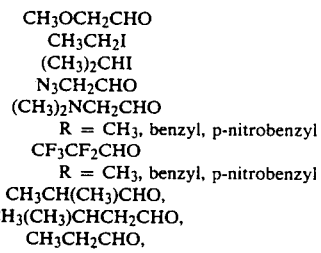

$CF_3CHO$,

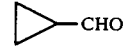

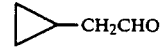

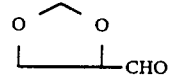

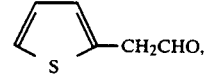

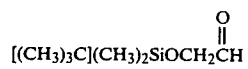

$[(CH_3)_3C](CH_3)_2SiOCH_2\overset{O}{\overset{\|}{C}}H$ $F_2CH\overset{O}{\overset{\|}{C}}H$ $FCH_2\overset{O}{\overset{\|}{C}}H$ -continued

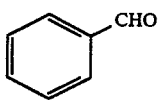

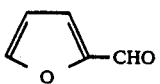

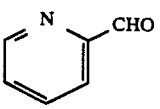

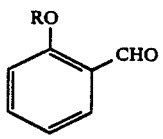

R = protecting group

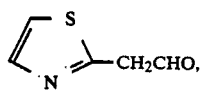

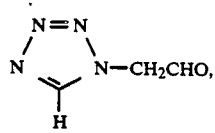

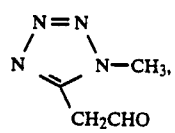

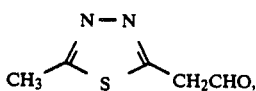

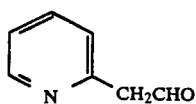

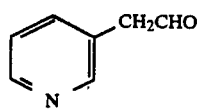

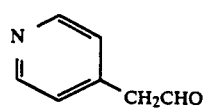

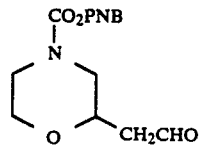

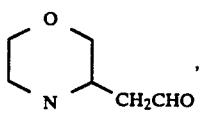

-continued

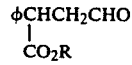

R is removable carboxyl protecting group, such as benzyl.

As mentioned above, the 6-substituents may also be established by acylation. Utilization of such acylating agents may be demonstrated in the following manner with regard to a preferred starting material Ib or Ic:

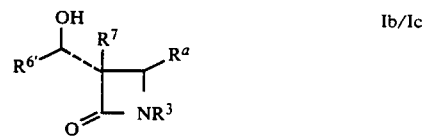

wherein $R^7$, $R^a$ and $R^3$ are as defined above. $R^{6'}$ is defined relative to the definition of $R^6$ and in that sense is the balance of the previously identified group $R^6$. In other words, for purposes of this definition $R^{6'}CH(OH)-=R^6$. An especially preferred material Ib is when $R^7$ is hydrogen and $R^{6'}$ is methyl. Basically, such 1'-hydroxy $R^{6'}$ species Ib are prepared according to the following scheme:

SCHEME II

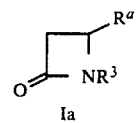

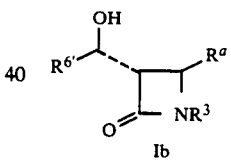  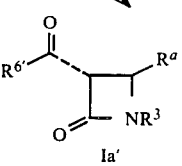

The alkylation Ia→Ib, Scheme II, is accomplished as previously described, by treating Ia in a solvent such as tetrahydrofuran, dimethoxyethane, diethylether, hexamethylphosphoramide, at a temperature of from −100° to −20° C. with a strong base such as lithium diisopropylamide, lithium hexamethyldisilazide, lithium 2,2,6,6-tetramethylpiperidide, potassium hydride or the like followed by the addition of an equivalent to 10 fold excess of an aldehyde. This reaction gives a mixture of isomers from which the desired trans-R form Ib can be conveniently separated by chromatography or crystallization.

Intermediate Ia may proceed directly to Ib as indicated above, or it may take the circuitous path via Ia'. The direct acylation, to Ia' is accomplished by treating Ia with two or more equivalents of a base such as lithium diisopropylamide, lithium hexamethyldisilazide, lithium 2,2,6,6-tetramethylpiperidide, in a solvent such as tetrahydrofuran, diethylether, or dimethoxyethane, for example, at a temperature of from −100° to −20° C. with an acylating agent such as N-acyl imidazole or the like. Addition of the Ia plus base mixture to the acylating agent is preferred.

Representative acylating agents for this scheme Ia-→Ia'→Ib are listed below.

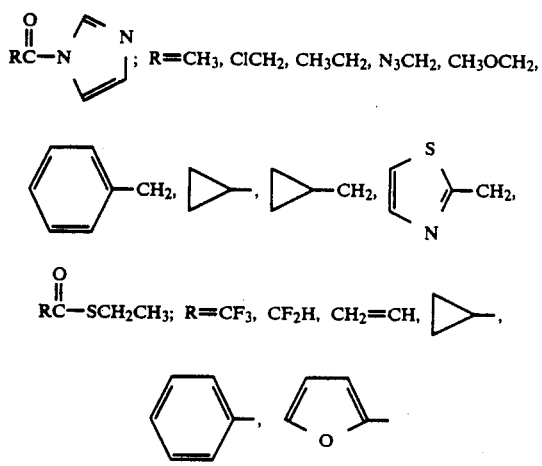

Further with respect to Scheme II, the reduction, Ia'→Ib is accomplished by contacting the ketone with a reducing agent such as potassium tri(sec-butyl)borohydride, lithium tri(sec-butyl) borohydride, sodium borohydride, sodium tris(methoxyethoxy)aluminum hydride, lithium aluminum hydride or the like in a solvent such as diethylether, tetrahydrofuran, toluene, i-propanol or the like at a temperature from −78° to 25° C. The reaction can conveniently be conducted in the presence of an added complexing salt such as potassium iodide, magnesium bromide or the like.

In a similar manner, unresolved Ib (cis and trans) may be oxidized to Ia' for reduction to Ib as indicated above:

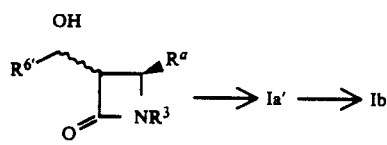

The oxidation is accomplished with an oxidizing agent such as dipyridine chromium (VI) oxide, trifluoroacetic anhydride-dimethylsulfoxidetriethylamine, pyridinium dichromate, acetic anhydride-dimethylsulfoxide in a solvent such as methylene chloride, acetonitrile, or the like at a temperature of from −78° to 25° C. for from 5 minutes to 5 hours.

Finally, relative to 6-substituents $R^6$ and $R^7$, it is to be emphasized that the most preferred class of compounds I is that wherein $R^7$ is hydrogen and $R^6$ is —CH(OH)CH$_3$, and wherein the absolute configuration is 5R, 6S, 6(R 1-hydroxyethyl) about carbon atoms 5 and 6:

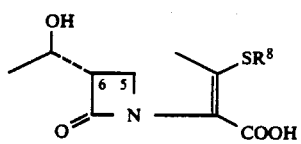

Other preferred values for $R^6$ ($R^7$=H) are: FCH$_2$CH(OH)—, CH$_3$CH$_2$CH(OH)—, CH$_3$CH$_2$—, and (CH$_3$)$_2$C(OH)—.

As noted above, the compounds of the present invention may also generally be represented by the following structural formula:

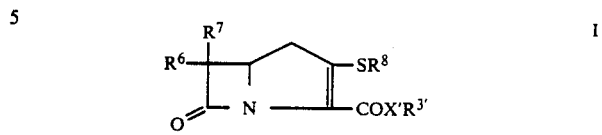

wherein X' is oxygen, sulfur NR' (R' is hydrogen or loweralkyl having from 1 to 6 carbon atoms); and $R^{3'}$ is hydrogen, or, inter alia, is representatively selected to provide the pharmaceutically acceptable salt, ester, anhydride ($R^{3'}$ is acyl), and amide moieties known in the bicyclic β-lactam antibiotic art; $R^{3'}$, may also be a readily removable blocking group.

Identification of the Radical —COX'R$^{3'}$

In the generic representation of the compounds of the present invention (I, above), the radical represented by COX'R$^{3'}$ is, inter alia, —COOH (X' is oxygen and $R^{3'}$ is hydrogen) and all radicals known to be effective as pharmaceutically acceptable ester, anhydride ($R^{3'}$ is acyl) and amide radicals in the bicyclic β-lactam antibiotic art, such as the cephalosporins and penicillins and nuclear analogues thereof.

Suitable blocking esters ($R^{3'}$, X=O) include those selected from the following list which is representative:

(i) $R^{3'}=CR^aR^bR^c$ wherein at least one of $R^aR^b$ and $R^c$ is an electron-donor, e.g., p-methoxyphenyl. The remaining $R^a$, $R^b$ and $R^c$ groups may be hydrogen or organic substituting groups. Suitable ester groups of this type include p-methoxybenzyloxycarbonyl.

(ii) $R^3=CR^aR^bR^c$ wherein at least one of $R^aR^b$ and $R^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) $R^{3'}=CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, diphenylmethoxycarbonyl and triphenylmethoxycarbonyl.

Silyl esters, under this category of blocking groups, may conveniently be prepared from a halosilane of the formula: $R_3^4SiX'$ wherein X' is a halogen such as chloro or bromo and $R^4$ is alkyl, e.g., methyl, ethyl, -butyl.

Pharmaceutically acceptable carboxyl derivatives of the present invention are those derived by reacting I with alcohols, acylating reagents and the like. For example, esters and amides of interest are the above-listed starting materials and final products having the —COX'R$^{3'}$ group at the 3-position; wherein X' is oxygen, sulfur or NR' (R' is H or R$^{3'}$), and $R^{3'}$ is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkylportion has 1-6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1-4 carbon atoms such, as 2-propenyl, 3-butenyl, and 4-butenyl; aralkyl and lower alkoxyl- and nitro- substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the $$-N\text{-group.}\atop R'$$

Representative of such amides are those wherein R' is selected from the group consisting of hydrogen and lower alkyl such as methyl and ethyl.

The most preferred —COX'R$^{3'}$ radicals of the present invention are those wherein (relative to Structure I above), X' is oxygen and R$^{3'}$ is hydrogen; loweralkyl having 1–4 carbon atoms; lower alkenyl such as 3-methylbutenyl, 4-butenyl and the like; benzyl and substituted benzyl such as p-nitrobenzyl; pivaoyloxymethyl, 3-phthalidyl; and phenacyl.

The compounds of the present invention (I) are valuable antibiotics active against various gram-positive and gram-negative bacteria and accordingly find utility in human and veterinary medicine. Representative pathogens which are sensitive to antibiotics I include: *Staphylococcus aureus, Escherichia coli, Klebsiella pneumoniae, Bacillus subtilis, Salmonella typhosa Psuedomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy and inhibit the growth of harmful bacteria in medical and dental equipment and as bactericides in industrial applications, for example in water-based paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueus vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg of body weight of the subject in one or more treatments per day. A preferred daily dosage for adult humans lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution. For zwitterionic species described under Structure I, the pH of such solutions typically will correspond to the zwitterionic point; however, consideration of individual properties of solubility and stability may require such aqueous solutions to have a pH other than that of the zwitterinic point, for example in the range of 5.5 to 8.2.

Incorporation by Reference

The following paragraphs summarize the previous incorporations.

The compounds of the present invention may also be prepared by the processes disclosed and claimed in the three (3) following, co-pending, commonly assigned, concurrently filed U.S. Patent Applications of Christensen, Ratcliffe and Salzmann. To the extent that these applications define R$^6$, R$^7$, and R$^8$ of Structure I and to the extent that they describe processes for the synthesis of I, they are hereby incorporated by reference.

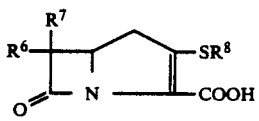

(1.) Process for the Preparation of 1-Carbapenems and Intermediates via 4-Allylazetidinone; U.S. patent application Ser. No. 134,408, filed Mar. 27, 1980; EPO Application 81102268.0 filed 3-26-81.

(2.) Process for the Preparation of 1-Carbapenems and Intermediates via Trithioorthoacetates; U.S. patent application Ser. No. 134,396, filed Mar. 27, 1980; EPO Application 81102269.8 filed 3-26-81.

(3.) Process for the Preparation of 1-Carbapenems and Intermediates via Silyl-Substituted Dithioacetals; U.S. patent application Ser. No. 134,397, filed Mar. 27, 1980; EPO Application 81102270.6 filed 3-26-81.

(4.) European Patent Application Ser. No. 80102076.9 filed Apr. 18, 1980.

Also incorporated by reference is published European Patent Application 0007614 (Application Number 79102615.6, filed July 24, 1979). This application discloses certain dipeptidase inhibitors which, on co-administration to mammalian subjects, enhance the efficacy of certain 1-carbadethiapenem antibiotics. Thus, to the extent that the cited application: (1.) defines the manner by which susceptible carbadethiapenems substrates of the present invention may be identifed; and (2.) dicloses suitable inhibitors, compositions, and methods of treatment, it is incorporated herein by reference. A particularly preferred inhibitor is 6-(L-2-Amino-2-carboxyethylthio)-2-(2,2-DCC)-2-hexenoic acid.

In the foregoing word description of the above schematic reaction diagram for the total synthesis of the defined carbapenem antibiotics, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. Temperature is in °C.

EXAMPLE 1

This example and those depending from it demonstrate the so called "carbamimidoyl" embodiments of I. As defined above, such carbamimidoyl embodiments are characterized by the following generic representation:

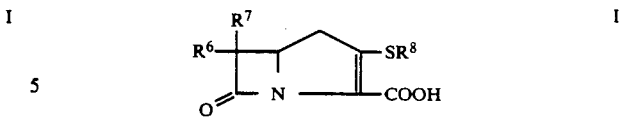

wherein:
$R^8$, characterized by the carbamimidoyl group, is defined above.

The following diagram summarizes the foregoing text, and is illustrative of a preferred procedure for making the carbamimidoyl embodiments. In the following scheme, the synthesis shows a subgeneric objective, since it is representative of the entire carbamimidoyl genus. Other subgeneric expressions and species members of the carbamimidoyls are obtained by analogy:

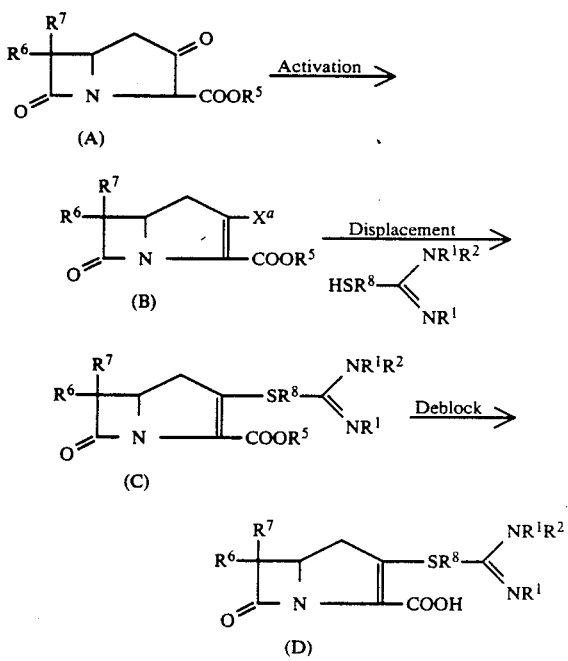

wherein: all symbols are as previously defined.

The activation step, A→B, which establishes the leaving group $X^a$ is accomplished by acylating the keto ester A with an acylating agent such as, for example, p-toluenesulfonic acid anhydride, trifluoromethanesulfonic acid anhydride, p-nitrophenylsulfonic acid anhydride, 2,4,6-triisopropylphenylsulfonic acid anhydride, methanesulfonic acid anhydride, diphenylchlorophosphate, toluenesulfonyl chloride, p-bromophenylsulfonyl chloride, or the like. The leaving group $X^a$ thus is established as the corresponding p-toluenesulfonyloxy, p-nitrophenylsulfonyloxy, diphenylphosphoryl, for example. Typically, the activation is carried out in suitable organic solvent such as methylene chloride, chloroform, acetonitrile, dimethylformamide, dichloromethane, tetrahydrofuran, and the like, in the presence of a base such as diisopropylethylamine, triethylamine, 4-dimethylaminopyridine, pyridine, and the like at a temperature of from $-20°$ to $40°$ C. The reaction usually is complete in from 0.5 to 5 hours.

The carboxyl protecting group $R^5$ in the keto ester, A, may be any of the well-known, readily removable carboxyl protecting groups such as, benzyl, p-nitrobenzyl, o-nitrobenzyl, methoxymethyl, allyl and the like.

The carbamimidoylthio side chain, B→C, is established by treating the activated keto ester, B, in a solvent such as dioxane, dimethylformamide, dimethylsulfoxide, acetonitrite, dichloromethane, tetrahydrofuran, hexamethylphosphoramide, and the like, in the presence of an approximately equivalent to excess quantity of the mercaptan reagent of choice in the presence of a base, such as diisopropylamine, triethylamine, pyridine, sodium hydrogen carbonate, potassium carbonate, and the like. The reaction is run at −40° to 50° C. and usually is complete in 5 minutes to 10 hours. Such mercaptan reagents are either known or readily prepared by known techniques.

The mercaptan reagent may be employed in the form of the free base (as described above), a salt such as the hydrochloride, the hydrobromide, the sulfate and the toluenesulfonate, or a nitrogen atom may be protected with a conventional N-blocking group such as p-nitrobenzyloxycarbonyl. When the mercaptan reagent is in the free base form, the displacement reaction does not require the presence of additional base.

The final deblocking step, C→D, preferably is carried out by catalytic hydrogenation. Catalysts suitable for the reaction include platinum metals, for example, platinum oxide, Pd/C, Pd(OH)$_2$, Pt/C, and the like which are employed with a hydrogen pressure of from 1 to 10 atmospheres at a temperature of from 0° to 25° C. in the presence of a solvent such as tetrahydrofuran, dioxane, water, and the like. The reductive deblocking step is usually carried out in the presence of a buffer such as pH 7 phosphate buffer or pH 7: MOPS-NaOH buffer. The reaction usually is complete in from 0.5 to 12 hours.

The following examples specifically demonstrate the process of Example 1.

EXAMPLE 2

(5R,6S)-2-(Carbamimidoylmethyl-1-thio)-6-(-1-R-hydroxyethyl)carbapen-2-em-3-carboxylic acid

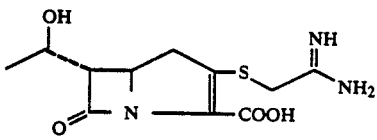

To a solution of (5R,6S)-P-nitrobenzyl-6-[(R)-1-hydroxyethyl]-1-azabicyclo[3.2.0]heptan-3,7-dione-2-carboxylate (34.8 mg) in dry acetonitrile (0.7 ml) at 0° is added simultaneously diphenylchlorophosphoridate (21.8 μl). The solution is stirred in an ice bath for 1 hour then a solution of 2 mercaptoacetamidine hydrochloride (15 mg) in dry dimethylsulfoxide (0.7 ml) is added dropwise simultaneously with diisopropylethylamine (25 μl) during a period of 8 minutes. After stirring 20 minutes at 0° the solution is poured into 40 ml of ether and centrifuged. The gummy precipitate is shaken twice with 10 ml portions of ether which are decanted. The residue of p-nitrobenzyl (5R,6S)-2-(carbamimidoylmethyl-1-thio)-6-(1-R-hydroxy-ethyl)carbapen-2-em-3-carboxylate is dissolved in 8 ml of tetrahydrofuranwater 1:1, pH 7 phosphate buffer (4 ml, 0.1M) is added and the solution is hydrogenated at 40 PSI in the presence of 25 mg of 10% Pd/C for 1 hour. The catalyst is removed by filtration and washed with 10 ml of water. The combined filtrates are extracted with ether (30 ml). The aqueous layer is concentrated to 5 ml and applied to a column of Dowex 50×4, (K$^+$ cycle) resin (30 ml). The column is eluted with water taking 9 ml portions. The product obtained in fractions 10–13 is combined, concentrated to 4 ml in vacuo at a bath temperature of 35° and freeze dried. Yield 11.3 mg (38%) U.V. max 295 mμ, E%291 (97% NH$_2$OH ext).

EXAMPLE 3

(5R,6S)-2-(N-Methylcarbamimidoylmethyl-1-thio)-6-(1-R-hydroxyethyl)carbapen-2-em-3-carboxylic acid

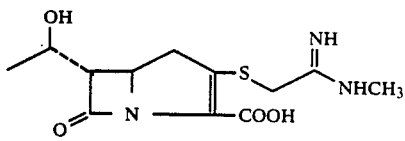

(5R,6S)-p-nitrobenzyl-6-[(R)-1-hydroxyethyl]-1-azabicyclo[3.2.0]heptan-3,7-dione-2-carboxylate (0.7 g) is dissolved in acetonitrile (14 ml). The solution is cooled in an ice-bath under nitrogen. Diphenyl-phosphorochloridate (0.44 ml) and diisopropylethylamine (0.42 ml) are added all at once. The reaction is complete in 20 minutes. To the solution of p-nitrobenzyl (5R,6S)-3-diphenylphosphoryl-6-[(R)-1-hydroxyethyl] 1-azabicyclo[3.2.0]hept-2-en-7-one-2-carboxylate thus obtained are added diisopropylethylamine (0.42 ml) and a solution of N-methyl-2-mercaptoacetamidine hydrochloride (0.35 g) in dimethylsulfoxide (8 ml) during a period of 5 minutes. The solution is poured into a flask containing 300 ml of ether with swirling, as the major portion of the product precipitates as a gum. The cloudy supernatant solution is filtered through a layer of "cellite" and the flask and filter pad are rinsed with ether. The gum on the filter is dissolved in 100 ml of THF-H$_2$O, 3:2 and the filtrate is added to the residue in the flask. pH 7 Phosphate Buffer (80 ml 0.1M) is added and the solution is hydrogenated at 50 PSI in the presence of 10% palladium on charcoal catalyst (0.7 g) for 1 hour 20 minutes. The catalyst is filtered and the filtrate is extracted with ether (100 ml). The aqueous layer is concentrated to 20 ml under vacuum and applied to a column (4 cm×36 cm) of Dowex 50×2 (K$^+$ cycle) resin in a cold room.

The column is eluted with water taking 28 ml fractions every 6 minutes. Fractions 25–55 are concentrated and freeze dried. Yield 210 mg U.V. max. 295 mμ, E% 169, 95% NH$_2$OH ext. Crystals from H$_2$O give λmax. 295, E% 241, 95% ext.

EXAMPLE 4

(5R,6S)-2-(N,N-Dimethylcarbamimidoylmethyl-1-thio)-6-(1-R-hydroxyethyl)carbapen-2-em-3-carboxylic acid

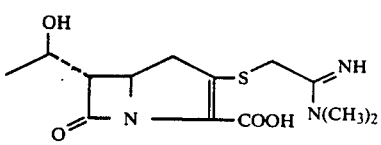

To a stirred solution of (5R,6S)-p-nitrobenzyl-6-[(R)-1-hydroxyethyl]-1-azabicyclo[3.2.0]-heptan-3,7-dione-2-carboxylate (1.45 g) in acetonitrile (20 ml) in an ice-bath under nitrogen is added diphenylchlorophosphate (0.88 ml) and diisopropylethylamine (0.84 ml) dropwise during 5 minutes. After 30 minutes, diisopropylethylamine (0.7 ml) and a solution of N,N-dimethyl-mercaptoacetamidine hydrochloride (0.82 g) in dimethylsulfoxide (12 ml) are added dropwise during 15 minutes. The solution is poured into ether (0.6 L) and the resulting gum is immediately taken up in a mixture of tetrahydrofuran 120 ml, water 40 ml, and 0.1M phosphate (pH 7, 140 ml) and hydrogenated for 2 hours at 50 PSIG in the presence of 1.4 g of 10% Pd/C catalyst. The catalyst is filtered and the filtrate is extracted with ether (250 ml). The aqueous layer is concentrated to 125 ml under vacuum and chromatographed on 600 ml of Dowex 50×2 (K+ cycle) resin, eluted with water. The fractions obtained between 1.1 L and 1.6 L of eluate are combined, concentrated and freeze dried. Yield 0.58 g (33%) U.V. λmax 295 nμ, E% 205, 94% $NH_2OH$ ext.

Following the above procedure, the following compound is obtained when the corresponding 9-fluoro starting material is substituted in equivalent amount:

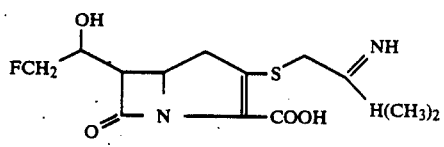

EXAMPLE 5

N,N-Dimethyl-2-chloroacetamidine Hydrochloride

Sodium (23 mg) is dissolved in methanol (40 ml) under an atmosphere of nitrogen. To the solution is added chloroacetonitrile (6.32 ml) followed after 30 minutes by dimethylamine hydrochloride (8.16 g). After stirring an additional hour the solution is concentrated to a small volume. Ether is added and the product which crystallizes is filtered and washed with ether, yielding 14.5 g of N,N-dimethylchloroacetamidine hydrochloride. NMR, 60 MHZ, $D_2O$, 3.23 and 3.37 $N(CH_3)_2$; 4.06 (S) $CH_2Cl$.

This process is found in *J. Med. Chem.*, 1979, Vol. 22, p. 295; William A. Bolhofer, Charles W. Habeckes, Adolph M. Pretruszkiewicz.

EXAMPLE 6

N,N-Dimethyl-2-mercaptoacetamidine Hydrochloride

A solution of N,N-dimethyl 2-chloroacetamidine hydrochloride (1.8 g), and trisodium phosphorothioate (2.2 g) in 15 ml of water is stirred at room temperature for one hour. Hydrochloric acid (12 ml, 1N) is added and the solution is heated at 90° for 30 minutes under an atmosphere of nitrogen. The solution is concentrated to a slurry of crystals and isopropanol is added. The mixture is filtered and the filtrate is evaporated to an oil. The residue is triturated several times with ether and finally residual solvents are removed on a vacuum pump leaving a gummy residue. This is recrystallized from ethanol ether. m.p. 157°–159°, 60 MHz, NMR, $D_2O$, 3.15 and 3.28 $(CH_3)_2$; 3.65 $CH_2SH$. See Bolhofer, et al., *J. Med. Chem.*, 1979, Vol. 22, p. 295.

EXAMPLE 7

Following the procedure in Examples 5 and 6, but using ethylamine hydrochloride there is obtained N-ethyl-2-mercaptoacetamidinium chloride 60 MHZ, NMR, $D_2O$, 1.3(t) $CH_2CH_3$; 3.42 $CH_2CH_3$; 3.62, (S), $CH_2SH$. Substituting 2-chloropropionitrile in gives R,S-2-mercapto propionamidine hydrochloride, NMR 1.64, (d), $CH_3$; 3.93, (q) CH, and R,S-N-methyl-2-mercaptopropionamidine hydrochloride, NMR, 1.61, d, $CH_3$; 3.0, $NCH_3$; 3.97, (q), $CHCH_3$.

EXAMPLE 8

Following the procedure of Example p-nitrobenzyl (5R, 6S)-3-diphenylphosphoryl-6-[(R)-1-hydroxyethyl]-1-azabicyclo[3.2.0]hept-2-en-7-o ne-2-carboxylate is reacted with the following mercapto carbamimidoyls to yield the corresponding carbamimidoyls I:

| Compound | $-SR^8$ | $HSR^8$ | % Yield | U.V. max. | E % | $NH_2OH$ ext |
|---|---|---|---|---|---|---|
| (1.) | S-CH(NH)-NH₂ | HS-CH(NH)-NH₂ | 26 | 294 mμ | 257 | 94% |
| (2.) | S-CH(NH)-NHCH₃ | HS-CH(NH)-NHCH₃ | 32 | 296 mμ | 232 | 95% |
| (3.) | S-CH(NH)-NHC₂H₅ | HS-CH(NH)-NHC₂H₅ | 23 | 294 mμ | 215 | 96% |
| (4.) | S-CH₂-C(NH)-NH₂ | HS-CH₂-C(NH)-NH₂ | 54 | 299 mμ | 271 | 96% |

EXAMPLE 6

Following the procedure of Examples 1-8, the following compounds I are obtained when an equivalent amount of the appropriately substituted bicyclic keto ester (A) is taken:

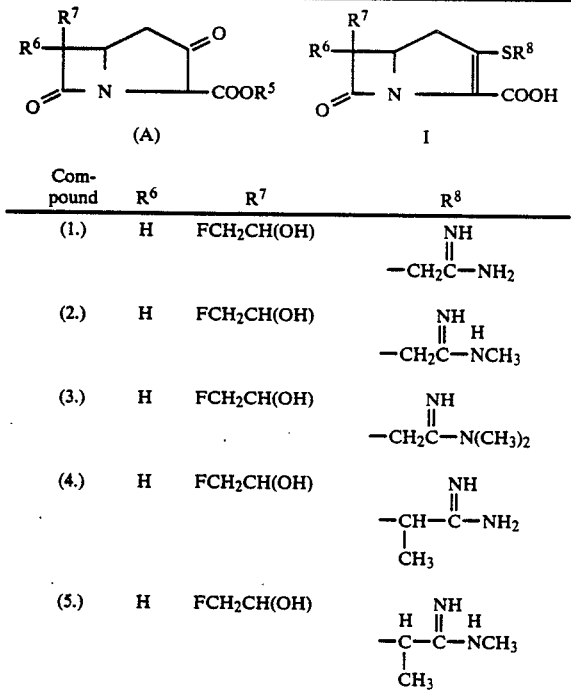

| Compound | $R^6$ | $R^7$ | $R^8$ |
|---|---|---|---|
| (1.) | H | $FCH_2CH(OH)$ | $-CH_2\overset{NH}{\overset{\|}{C}}-NH_2$ |
| (2.) | H | $FCH_2CH(OH)$ | $-CH_2\overset{NH}{\overset{\|}{C}}\overset{H}{-NCH_3}$ |
| (3.) | H | $FCH_2CH(OH)$ | $-CH_2\overset{NH}{\overset{\|}{C}}-N(CH_3)_2$ |
| (4.) | H | $FCH_2CH(OH)$ | $-\underset{CH_3}{\underset{\|}{CH}}-\overset{NH}{\overset{\|}{C}}-NH_2$ |
| (5.) | H | $FCH_2CH(OH)$ | $-\underset{CH_3}{\underset{\|}{\overset{H}{C}}}-\overset{NH}{\overset{\|}{C}}\overset{H}{-NCH_3}$ |
| (6.) | H | $FCH_2CH(OH)$ | $-CH_2\overset{NH}{\overset{\|}{C}}\overset{H}{-NCH_2CH_3}$ |
| (7.) | H | $FCH_2CH(OH)$ | $-CH_2CH_2\overset{NH}{\overset{\|}{C}}-NH_2$ |
| 8-14 | | | Compounds 8-14 correspond sequentially to Compound 1-7 of Table 9 when the value of $R^7 = FCH_2CH(OH$ is changed to $CH_3CH_2CH(OH)$. |
| 15-21 | | | Compound 15-21 correspond sequentially to Compound 1-7 of Table 9 when the value of $R^7 = FCH_2CH(OH)$ is changed to $CH_3CH_2$. |
| 22-28 | | | Compound 22-28 correspond sequentially to Compound 1-7 of Table 9 when the Value of $R^7 = FCH_2CH(OH)$ is changed to $(CH_3)_2C(OH)-$. |

EXAMPLE 10

Following the procedure of the foregoing text and examples, the following "carbamimidoyl" embodiments of the present invention are obtained.

| Compound | $R^6$ | $R^7$ | $-SR^8$ |
|---|---|---|---|
| 1 | H | $\underset{CH_3CH-}{\overset{OH}{\|}}$ | $-SCH_2-\overset{NCH_3}{\overset{\|}{C}}-NHCH_3$ |
| 2 | H | $\underset{CH_3CH-}{\overset{OH}{\|}}$ | $-SCH_2-\overset{NCH_3}{\overset{\|}{C}}-N(CH_3)_2$ |
| 3 | H | $\underset{CH_3CH-}{\overset{OH}{\|}}$ | $-SCH_2-\overset{\overset{\oplus}{N(CH_3)_2}}{\overset{\|}{C}}-N(CH_3)_2$ |
| 4 | H | $\underset{CH_3CH-}{\overset{OH}{\|}}$ | $-SCH_2-\overset{NH}{\overset{\|}{C}}-\underset{CH_3}{\underset{\|}{N}}-C_2H_5$ |
| 5 | H | $\underset{CH_3CH-}{\overset{OH}{\|}}$ | $-S-CH_2\overset{NH}{\overset{\|}{C}}-N(C_2H_5)_2$ |
| 6 | H | $\underset{CH_3CH-}{\overset{OH}{\|}}$ | $-SCH_2-\overset{NH}{\overset{\|}{C}}-NCH(CH_3)_2$ |
| 7 | H | $\underset{CH_3CH-}{\overset{OH}{\|}}$ | $-SCH_2-\overset{NH}{\overset{\|}{C}}-NC(CH_3)_3$ |

-continued

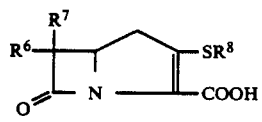

| Compound | R⁶ | R⁷ | —SR⁸ |
|---|---|---|---|
| 8 | H | CH₃CH(OH)— | —SCH(CH₃)—C(=NH)—N(CH₃)₂ |
| 9 | H | CH₃CH(OH)— | —SCH₂—C(=NH)—NH₂ (with φ substituent) |
| 10 | H | CH₃CH(OH)— | —S—C(=CH₂)—C(=NH)—NH₂ |
| 11 | H | CH₃CH— | —S—CH(CH=CH₂)—C(=NH)—NH |
| 12 | H | CH₃CH(OH)— | —S—CH₂CH(OCH₃)—C(=NH)—NH₂ |
| 13 | H | CH₃CH(OH)— | —SCH₂—CH(OH)—C(=NH)—NH₂ |
| 14 | H | CH₃CH(OH)— | —S—CH₂—C(=NOCH₃)—C(=NH)—NH₂ |
| 15 | H | CH₃CH(OH)— | —SCH₂—CH(N(CH₃)₂)—C(=NH)—NH₂ |
| 16 | H | CH₃CH(OH)— | —SCH₂—CH(N⁺(CH₃)₃ Cl⁻)—C(=NH)—NH₂ |
| 17 | H | CH₃CH(OH)— | —S—CH₂—CH(SCH₃)—C(=NH)—NH₂ |
| 18 | H | CH₃CH(OH)— | —S—CH₂—C(=NH)—NHφ |
| 19 | H | CH₃CH(OH)— | SCH₂—C(=NOCH₃)=NH |
| 20 | H | CH₃CH(OH)— | S—CH₂CH₂CH₂—C(=NH)—NH₂ |

-continued

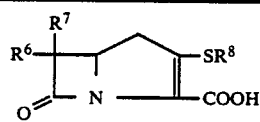

| Compound | R[6] | R[7] | —SR[8] |
|---|---|---|---|
| 21 | H | CH₃CH(OH)— | SCH₂—C(CH₃)(CH₃)—C(=NH)—NH₂ |
| 22 | H | CH₃CH(OH)— | SCH₂CH₂—C(=NH)—N(CH₃)₂ |
| 23 | H | CH₃CH(OH)— | —SCH₂—C(=NH)—N-pyrrolidinyl |
| 24 | H | CH₃CH(OH)— | SCH₂—C(=NH)—N-morpholinyl |
| 25 | H | CH₃CH(OH)— | SCH₂—C(=NH)—N-piperidinyl |
| 26 | H | CH₃CH(OH)— | SCH₂—C(=NH)—N(4-methylpiperazinyl) |
| 27 | H | CH₃CH(OH)— | —SCH₂—C(=NH)—NHCH₂φ |
| 28 | H | CH₃CH(OH)— | —SCH₂—C(=NH)—NHCH₂(2-pyridyl) |
| 29 | H | CH₃CH(OH)— | SCH₂—C(=NH)—NH—CH₂(3-pyridyl) |
| 30 | H | CH₃CH(OH)— | —S—CH₂—C(=NH)—NH—CH₂(4-pyridyl) |
| 31 | H | CH₃CH(OH)— | —S—CH₂—(1-methylbenzimidazol-2-yl) |
| 32 | H | CH₃CH(OH)— | —S—CH₂—C(=NH)—NH(2-pyridyl) |
| 33 | H | CH₃CH(OH)— | —S—CH₂—C(=NH)—NHN(CH₃)₂ |

-continued $$\text{structure with } R^6, R^7 \text{ on β-lactam ring, } SR^8 \text{ and COOH on carbapenem}$$

| Compound | R⁶ | R⁷ | —SR⁸ |
|---|---|---|---|
| 34 | H | CH₃CH(OH)— | —S—CH₂—C(=NH)—N(CH₃)—N(CH₃)₂ |
| 35 | H | CH₃CH(OH)— | —S—CH₃—C(=NH)—N(CH₃)—NHCH₃ |
| 36 | H | CH₃CH(OH)— | —S—CH₂—C(CH₃)(=NH)—N(CH₃)—N(CH₃)₂ |
| 37 | H | CH₃CH(OH)— | —S—CH₂—C(=NH)—N(CH₃)—O—CH₃ |
| 38 | H | CH₃CH(OH)— | —S—CH(C₂H₅)—C(=NH)—NH₂ |
| 39 | H | CH₃CH(OH)— | —S—CH(C₂H₅)—C(=NH)—N(CH₃)₂ |
| 40 | H | CH₃CH(OH)— | —S—CH(CH₃)—CH₂—C(=NH)—NH₂ |
| 41 | H | CH₃CH(OH)— | —S—CH₂—CH(CH₃)—C(=NH)—NH₂ |
| 42 | H | CH₃CH(OH)— | —S—CH₂—(2-imidazolin-2-yl, NH) |
| 43 | H | CH₃CH(OH)— | —SCH₂—(1-methyl-2-imidazolin-2-yl) |
| 44 | H | CH₃CH(OH)— | —SCH₂—C(=NCH₃)—N(pyrrolidinyl) |
| 45 | H | CH₃CH(OH)— | —SCH₂—C(=NCH₂CH₃)—N(CH₃)₂ |
| 46 | H | CH₃CH(OH)— | (2-methylamino-1-pyrrolin-3-yl)thio |

-continued

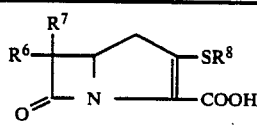

| Compound | $R^6$ | $R^7$ | $-SR^8$ |
|---|---|---|---|
| 47 | H | CH$_3$—CH(OH)— | (tetrahydropyrrolo-imidazoline-2-thio) |
| 48 | H | CH$_3$—CH(OH)— | S—CH$_2$—(N-methyl-tetrahydropyrimidin-2-ylidene) |
| 49 | H | CH$_3$—CH(OH)— | SCH$_2$—(1-carboxymethyl-imidazolin-2-yl) |
| 50 | H | CH$_3$—CH(OH)— | —SCH=CH—C(=NH)—NH$_2$ |
| 51 | H | CH$_3$—CH(OH)— | —SCH=CH—C(=NH)—N(CH$_3$)$_2$ |
| 52 | H | CH$_3$—CH(OH)— | —SC(CH$_3$)=CH—C(=NH)—NH$_2$ |
| 53-104 | Compounds 53-104 correspond to Compounds 1-52 of Example 10 except that the value of $R^7$ as CH$_3$CH(OH) is FCH$_2$CH(OH)—. | | |
| 105-155 | Compounds 105-155 correspond to Compounds 1-52 of Example 10 except that the value of $R^7$ as CH$_3$CH(OH) is CH$_3$CH$_2$CH(OH). | | |
| 156-207 | Compounds 156-207 correspond to Compounds 1-52 of Example 10 except that the value of $R^7$ as CH$_3$CH(OH) is CH$_3$CH$_2$. | | |
| 208-259 | Compounds 208-259 correspond to Compounds 1-52 of Example 10 except that the value of $R^7$ as CH$_3$CH(OH) is (CH$_3$)$_2$C(OH)—. | | |

EXAMPLE 11

Preparation of Pharmaceutical Compositions

One such unit dosage form is prepared by mixing 120 mg of the compound of Example 4 (Compound A) with 20 mg of lactose and 5 mg of magnesium stearate and placing the 145 mg mixture into a No. 3 gelatin capsule. Similarly, by employing more of the active ingredient and less lactose, other dosage forms can be put in No. 3 gelatin capsules, and, should it be necessary to mire more than 145 mg of ingredients together, larger capsules such as compressed tablets and pills can be prepared. The following examples are illustrative of the preparation of pharmaceutical formulations:

| TABLET | PER TABLET |
|---|---|
| Compound A | 125 mg |
| Cornstarch, U.S.P. | 6 mg. |
| Dicalcium Phosphate | 192 mg. |
| Lactose, U.S.P. | 190 mg. |

-continued

| TABLET | PER TABLET |
|---|---|
| Magnesium Stearate | Balance/800 mg. |

The active ingredient is blended with the dicalcium phosphate, lactose and about half of the cornstarch. The mixture is then granulated with 15% cornstarch paste (16 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION Ampoule | |
| Compound A | 500 mg. |
| Diluent: Sterile Water for Injection | 2 cc. |
| OPTHALMIC SOLUTION | |
| Compound A | 100 mg. |

| -continued | |
|---|---|
| | PER TABLET |
| Hydropropylmethyl Cellulose | 5 mg. |
| Sterile Water to | 1 ml |
| OTIC SOLUTION | |
| Compound A | 100 mg. |
| Benzalkonium chloride | 0.1 mg |
| Sterile Water to | 1 ml. |
| TOPICAL OINTMENT | |
| Compound A | 100 mg. |
| Polyethylene Glycol 4000 U.S.P. | 400 mg. |
| Polyethylene Glycol 400 U.S.P. | 1.0 gram |

What is claimed is:

1. A compound having the formula:

$$\begin{array}{c} R^7 \\ R^6 \end{array}\begin{array}{c} \\ \\ \end{array}\begin{array}{c} SR^8 \\ \\ \end{array}$$
$$O= \quad N$$
$$\quad COOH$$

and the pharmaceutically acceptable salt, ester and amide derivatives thereof; wherein:

$R^6 = H$; and $R^7 =$ $$CH_3\overset{OH}{\underset{|}{CH}}-;\ \overset{OH}{\underset{|}{CH_2}};\ CH_3\overset{F}{\underset{|}{CH}}-;\ \text{or}\ FCH_2-\overset{OH}{\underset{|}{CH}}-;\ \text{and}$$

$R^8$ is selected from the group consisting of:

$$S-CH_2-\overset{N-C_2H_5}{\underset{\|}{C}}-NH_2$$

$$S-CH_2-\overset{NH}{\underset{\|}{C}}-\overset{NCH_3}{\underset{|}{N}}$$
$$\qquad\qquad\qquad C_2H_5$$

$$S-CH_2-\overset{NH}{\underset{\|}{C}}-N(C_2H_5)_2$$

$$S-CH_2-\overset{NH}{\underset{\|}{C}}-\overset{H}{\underset{|}{N}}C-(CH_3)_3$$

$$S-CH_2-\overset{NH}{\underset{\|}{C}}-NH_2$$

$$S-CH_2-\overset{NH}{\underset{\|}{C}}-NHCH_3$$

$$S-CH_2-\overset{NH}{\underset{\|}{C}}-N(CH_3)_2$$

$$S-CH_2-\overset{NCH_3}{\underset{\|}{C}}-NHCH_3$$

$$S-\overset{NH}{\underset{\|}{CH}}-\overset{}{\underset{|}{C}}-NH_2$$
$$\quad CH_3$$

$$S-\overset{NH}{\underset{\|}{CH}}-\overset{}{\underset{|}{C}}-NHCH_3$$
$$\quad CH_3$$

$$S-CH_2-\overset{NCH_3}{\underset{\|}{C}}-N(CH_3)_2$$

$$S-\overset{NH}{\underset{\|}{CH}}-\overset{}{\underset{|}{C}}-N(CH_3)_2$$
$$\quad CH_3$$

$$S-\overset{NH}{\underset{\|}{CH}}-\overset{}{\underset{|}{C}}-NH_2$$
$$\quad \phi$$

$$S-\overset{NH}{\underset{\|}{C}}-\overset{}{\underset{\|}{C}}-NH_2$$
$$\quad CH_2$$

$$S-\overset{NH}{\underset{\|}{CH}}-\overset{}{\underset{|}{C}}-NH_2$$
$$\quad CH=CH_2$$

$$S-CH_2-CH_2-\overset{NH}{\underset{\|}{C}}-NH_2$$

$$S-CH_2-CH_2-\overset{NH}{\underset{\|}{C}}-NH_2$$
$$\qquad\qquad\qquad\overset{|}{O}CH_3$$

$$S-CH_2-\overset{}{\underset{|}{CH}}-\overset{NH_2}{\underset{\diagdown}{C}}\diagup$$
$$\quad OH \qquad NH_2$$

$$S-CH_2-\overset{}{\underset{|}{CH}}-\overset{NH}{\underset{\|}{C}}-NH_2$$
$$\qquad\quad N(CH_3)_2$$

$$S-CH_2-\overset{NH}{\underset{\|}{C}}-N(CH_3)_2$$
$$\qquad\overset{|}{CO_2H}$$

$$S-CH-C=NH_2$$
$$\underset{|}{S} \quad \underset{|}{NH_2}$$
$$CH_3$$

$$S-CH_2-\overset{NH}{\underset{\|}{C}}-NH\phi$$

$$S-(CH_2)_n-\overset{NR^2}{\underset{\diagdown}{C}}\diagup$$
$$\qquad\qquad NHR^1 \quad n = 2-5,\ R^2 = H,\ CH_3$$
$$\qquad\qquad\qquad\qquad\qquad R^1 = H,\ CH_3$$

$$SCH_2\overset{CH_3}{\underset{|}{C}}\diagup\overset{NH}{\diagdown}$$
$$\quad\overset{|}{CH_3} \quad NH_2$$

-continued
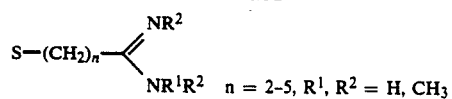   n = 2-5, R¹, R² = H, CH₃
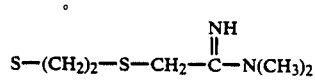
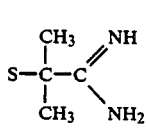
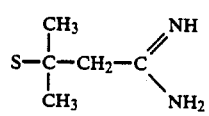
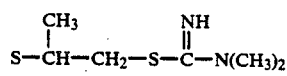
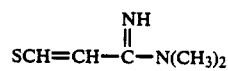
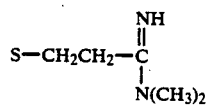
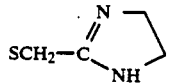
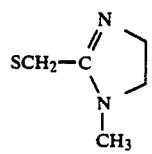
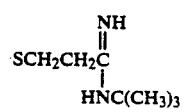
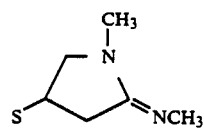
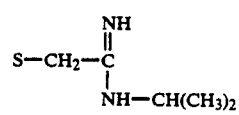
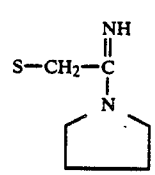
-continued
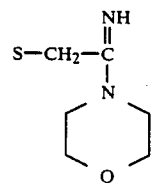
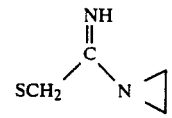
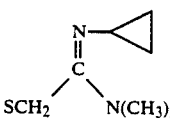
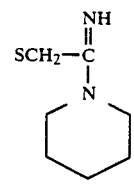
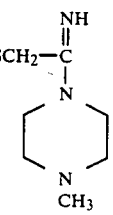
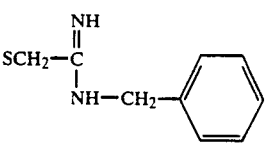
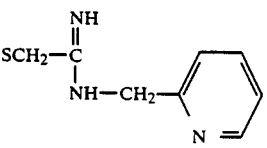
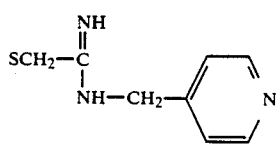
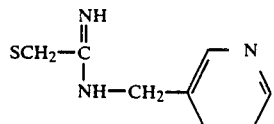
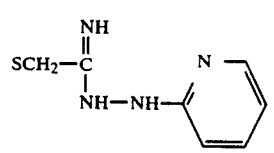

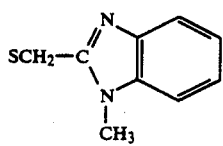
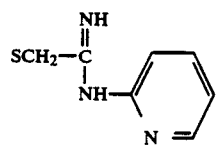
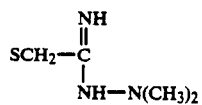
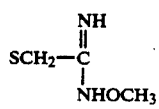
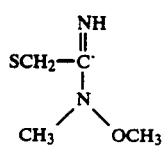
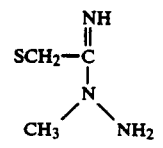
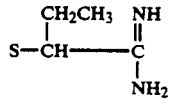
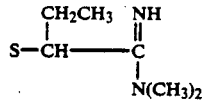
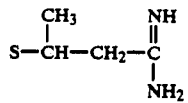
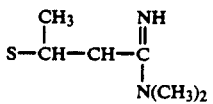
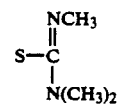
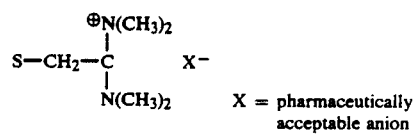
X = pharmaceutically acceptable anion
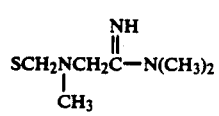
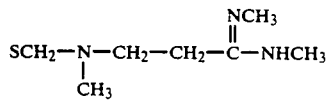
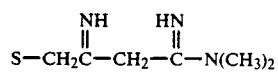
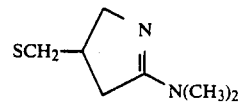
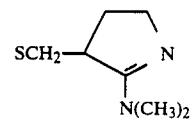
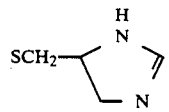
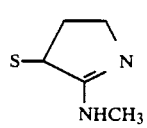
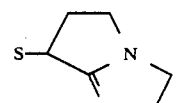
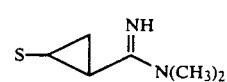
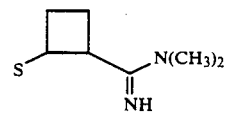
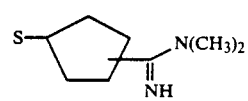
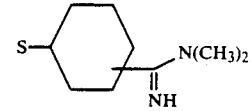
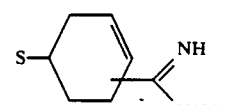
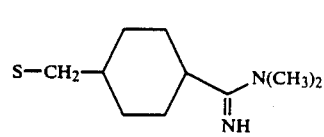

-continued
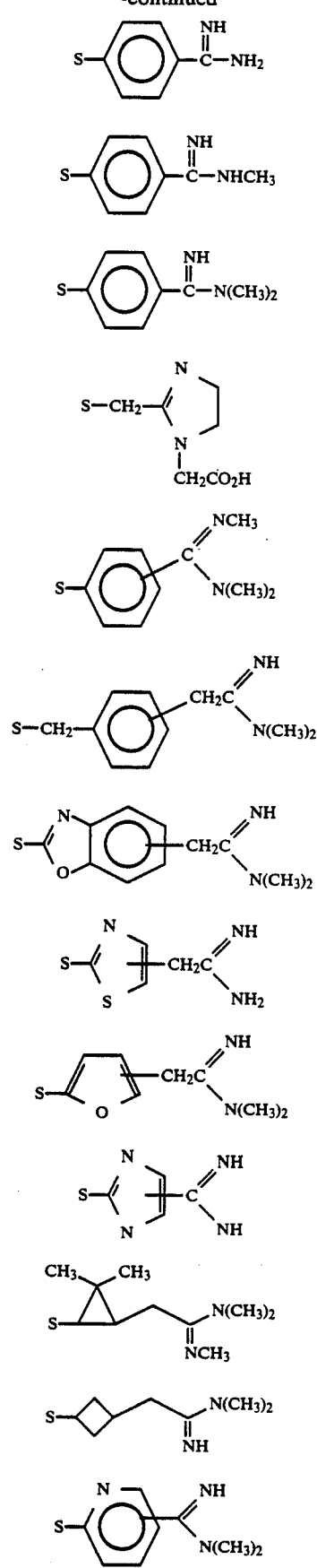
-continued
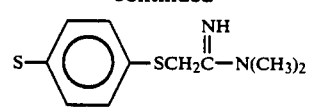
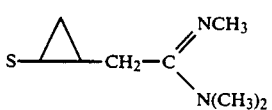
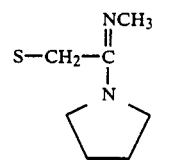
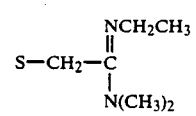
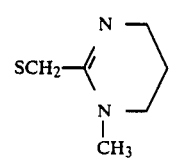 R$^1$ = H, CH$_3$
R$^2$ = H, CH$_3$
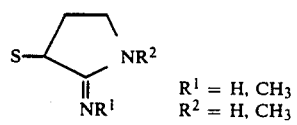 R$^1$ = H, CH$_3$
R$^2$ = H, CH$_3$
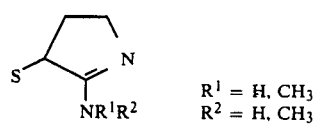
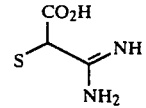
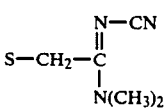
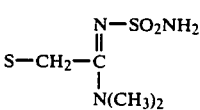 R$^1$ = CH$_3$
R$^2$ = CH$_3$, NR$^2$, OR
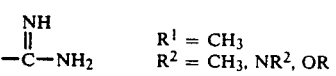 R$^1$ = H, CH$_3$
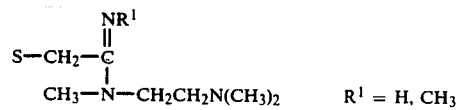 R$^1$ = H, CH$_3$
R$^2$ = H, CH$_3$
n = 1 or 2

-continued
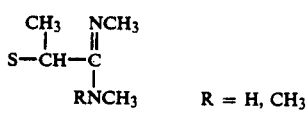   R = H, CH₃
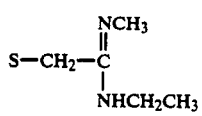
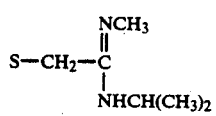
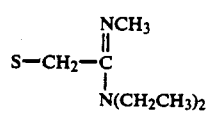
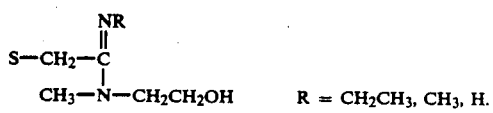   R = CH₂CH₃, CH₃, H.
-continued
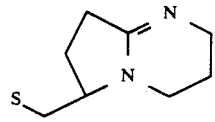
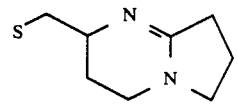
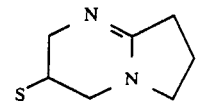
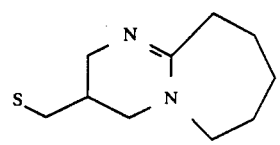
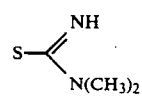
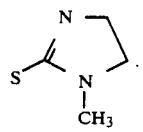
* * * * *